United States Patent [19]
Fletcher et al.

[11] 3,957,037
[45] May 18, 1976

[54] READOUT ELECTRODE ASSEMBLY FOR MEASURING BIOLOGICAL IMPEDANCE

[76] Inventors: James C. Fletcher, Administrator of the National Aeronautics and Space Administration, with respect to an invention of Leslie D. Montgomery, Mountain View; Dwight L. Moody, Jr., Saratoga, both of Calif.

[22] Filed: Feb. 24, 1975

[21] Appl. No.: 552,454

[52] U.S. Cl. ...................... 128/2.1 E; 128/2.05 V; 128/2.1 Z; 128/DIG. 4
[51] Int. Cl.² .......................................... A61B 5/04
[58] Field of Search ............ 128/2.1 E, 2.1 Z, 2.1 R, 128/2.06 E, 2.05 V, DIG. 4, 384, 404, 410, 411, 416–418

[56] References Cited
UNITED STATES PATENTS

| | | | |
|---|---|---|---|
| 431,978 | 7/1890 | Jackson | 128/418 |
| 3,398,740 | 8/1968 | Figar | 128/2.05 V |
| 3,476,104 | 11/1969 | Davis | 128/2.06 E |
| 3,517,661 | 6/1970 | Buffington | 128/2.05 V |
| 3,542,010 | 11/1970 | Love | 128/2.1 E |
| 3,545,430 | 12/1970 | Figar | 128/2.05 V |
| 3,659,614 | 5/1972 | Jankelson | 128/DIG. 4 |
| 3,831,589 | 8/1974 | Deering et al | 128/2.1 E |

FOREIGN PATENTS OR APPLICATIONS

| | | | |
|---|---|---|---|
| 732,130 | 9/1932 | France | 128/416 |
| 687,916 | 1/1940 | Germany | 128/2.1 R |
| 483,949 | 6/1927 | Germany | 128/404 |

Primary Examiner—Robert W. Michell
Assistant Examiner—Lee S. Cohen
Attorney, Agent, or Firm—Darrell G. Brekke; Armand G. Morin; John R. Manning

[57] ABSTRACT

The invention comprises of a pair of readout ring electrodes which are used in conjunction with apparatus for measuring the electrical impedance between different points in the body of a living animal to determine the amount of blood flow therebetween. The readout electrodes have independently adjustable diameters to permit attachment around different parts of the body between which it is desired to measure electric impedance. The axial spacing between the electrodes is adjusted by a pair of rods which have a first pair of ends fixedly attached to one electrode and a second pair of ends slidably attached to the other electrode. Indicia are provided on the outer surface of the ring electrodes and on the surface of the rods to permit measurement of the circumference and spacing between the ring electrodes. The ring electrodes are electrically isolated from each other.

7 Claims, 2 Drawing Figures

READOUT ELECTRODE ASSEMBLY FOR MEASURING BIOLOGICAL IMPEDANCE

ORIGIN

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

The invention generally relates to plethysmography which is the measurement of the size of an organ or limb and in the amount of blood flowing therein. More particularly, the invention relates to impedance plethysmography and the synonymous terms of bioimpedance, bioelectrical impedance, and impedance rheometry in which a pair of transmitting ring electrodes are used to apply a high frequency electric current to a patient and pair of readout ring electrodes are used to receive the varying high frequency electric current flowing through the part of the patient located between the transmitting ring electrodes and the readout ring electrodes associated therewith. The current flow between the transmitting and associated ring electrodes is a function of the variation of the electrical impedance therebetween. The electrical impedance in turn is a function of the variation of blood flow through the part of the patient encircled by the transmitting and receiving ring electrodes.

DESCRIPTION OF THE PRIOR ART

In the past, two types of electrical plethysmographic systems were developed. The first type is the capacitive plethysmograph which uses a single ring electrode spaced apart from a part of the body it encircles. The ring electrode forms one plate of a capacitor in which air is the dielectric and the other plate is the surface of the body which is encircled by the electrode. The pulsation of blood flowing through the part of the body encircled by the single ring electrode causes a cyclical variation in the capacitance existing between the body and the single ring electrode which is a function of the rate of flow of blood through the part of the body encircled by the ring electrode. U.S. Pat. Nos. 3,381,682, 3,398,740 and 3,545,430 are exemplary of capacitive plethysmograph systems.

The second type of electrical plethysmograph is known as the impedance plethysmograph. In the impedance plethysmograph, a high frequency electrical current is applied to the body to produce the flow of high frequency electrical current through the body to an associated pick up electrode. The variation in the electrical current flowing through the body is detected as an electrical impedance variation which is a function of the flow of blood through the body.

Two types of impedance plethysmographs have been developed. The first type is known as the bi-polar electrode system and the second type is known as the tetra-polar system. The bi-polar electrode system uses two rings disposed around a section of the body through which it is desired to measure blood flow. Each ring is used simultaneously as a transmitting and a readout electrode. A high frequency source of electrical current is applied to the electrodes to cause a current flow through the body between the two electrodes. A high input impedance amplifier is connected across the two electrodes to amplify the variation in voltage drop between the electrodes. The output of the high impedance amplifier is detected as an impedance output signal. The tetra-polar electrode system utilizes a pair of transmitting electrodes for applying a high frequency electrical current to a section of the body encircled by the electrodes. A pair of readout electrodes associated with the transmitting electrodes encircle a section of the body located between the transmitting electrodes to receive the current flowing through the section of the body located between the transmitting and associated readout electrodes. The output signal from the readout electrodes is amplified by a high input impedance and detected to produce an impedance output signal. U.S. Pat. No. 3,345,867 is exemplary of a tetra-polar impedance plethysmograph.

A publication entitled "Introduction to Bioimpedance Measurements" published as part of the Beckman Information Series CZ-1000, copyright 1973, may be referred to for a more complete description of the theory of operaion of bi-polar and tetra-polar systems.

There were at least two types of readout electrode constructions used in the prior art. In the first type, the two readout electrodes were constructed from two tin foil strips applied circumferentially around part of the body and held in place by alligator clips or other clamping arrangements. The alligator clips or other clamping arrangements served as the electrode lead connections. A conductive paste was applied between the tin foil strip and skin surface to insure electrical contact therewith.

A second type of readout electrode construction is disclosed in U.S. Pat. No. 3,335,867, supra, which consists of braided copper wire electrodes.

The prior art readout electrodes assemblies discussed above have numerous disadvantages. The electrode strips must be applied singly. The electrode strips are cumbersome to apply and are very difficult to reapply to the exact same location of the body to which they were applied for previous tests. The circumference of each electrode and the distance between the electrodes must be measured manually in order to obtain the volume of the body segment being studied. The parallel allignment of the two electrodes around a section of the body has been extremely difficult.

SUMMARY OF THE INVENTION

The invention comprises of a pair of readout ring electrodes which are adapted to be positioned around a segment of the body through which it is desired to study the rate of blood flow by measuring electrical impedance. The circumference of the rings is adjustable and is determined by a band encircling each of the electrode rings which have a hole tapped therein for engaging a set screw used for clamping the ring electrodes at a fixed circumference. Marking indicia are inscribed on the outside surface of the individual ring electrodes to permit a visual determination of the ring electrodes' circumference. The ring electrodes are held in a fixed axial position by a pair of rods having first and second ends. The first ends of the rods are fixedly joined to one of the ring electrodes by means of a pair of bushings which are mounted within a pair of cylindrical recesses connected to the outside surface of the first ring electrode. The second ends of the rods are slidably connected to the second ring electrode by means of a pair of bushings which are disposed within a pair of cylindrical recesses connected to the outside surface of the second ring electrode. A pair of nonconduting set screws are engaged in holes tapped through the cylindrical recesses and bushings of the second ring electrode to permit axial adjustment of the rods with respect to the second ring electrode by selective sliding of the rods with respect to the second ring electrode. The bushings are nonconductive to maintain electrical isolation between the first and second ring electrodes. The rods have measurements indicia inscribed on their outer surface to permit a visual determination of the axial displacement between the first and second ring electrodes. The output leads are attached to the ring electrodes by means of a pair of male connectors which are respectively inserted into a cylindrical recess sunk in the head of the set screws which are used for clamping the diameter of the first and second ring electrodes in a fixed position.

The disadvantages of and limitations of the prior art readout electrodes used in tetra-polar electrode systems are obviated by the present invention which has the following advantages. The readout electrodes may be easily applied to any segment of the body through which blood flow is being investigated. The provision of measurement indicia on the outside surface of the ring electrodes and on the rods permits circumference and axial displacement measurements to be made with great facility. The adjustability of the circumference of the ring electrodes and the axial displacement between them permits the reproduction of the exact electrode placement that has been used in previous studies. The male connectors produce an electrical contact having high continuity. The axial adjustment bars hold the ring electrodes rigid to minimize the effects of body movements in the output impedance signal.

DETAILED DESCRIPTION OF THE INVENTION

Figure 1:
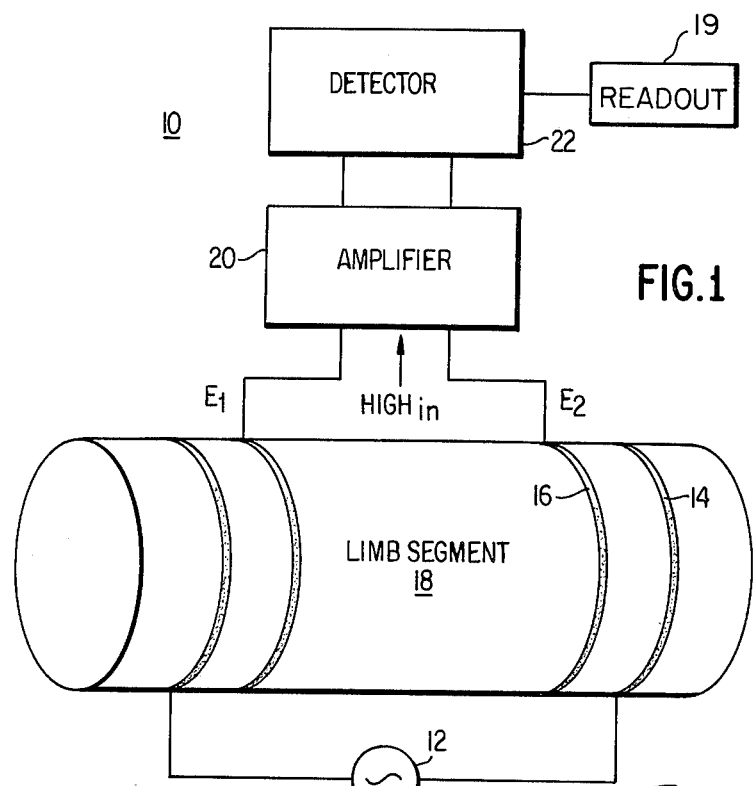
FIG. 1 is a schematic view of the electronic subsystem used in an impedance plethysmograph system which includes a pair of readout ring electrodes of the general type which form the subject matter of the present invention.

A tetra-polar electrode system using a pair of readout ring electrodes of the same general type as those which comprise the subject matter of the present invention is illustrated in FIG. 1. The system includes a source of high frequency electrical current 12. The high frequency source of electrical current 12 may be constructed from a constant current generator or constant voltage generator of well known construction. The constant current generator is preferred because it has been found to produce less electrical noise in the output signal than if the constant voltage generator is used. A commercially available system utilizing a constant current generator is the Beckman BR-100 bilateral impedance rheograph. The output signal from the high frequency electrical generator 12 is coupled to a pair of transmitting ring electrodes 14 which are disposed around a body segment 18. A pair of readout electrodes 16 are also disposed around the body segment 18. The output signal from the readout electrodes 16 is coupled to an amplifier 20 of a well known construction. The output of amplifier 20 is coupled to an impedance detector 22 of well known construction which produces an output signal which is a function of the electrical impedance existing between the transmitting electrodes 14 and the associated readout ring electrodes 16. The output signal is monitored by readout 19 which may be, for example, a recorder or meter.

Figure 2:
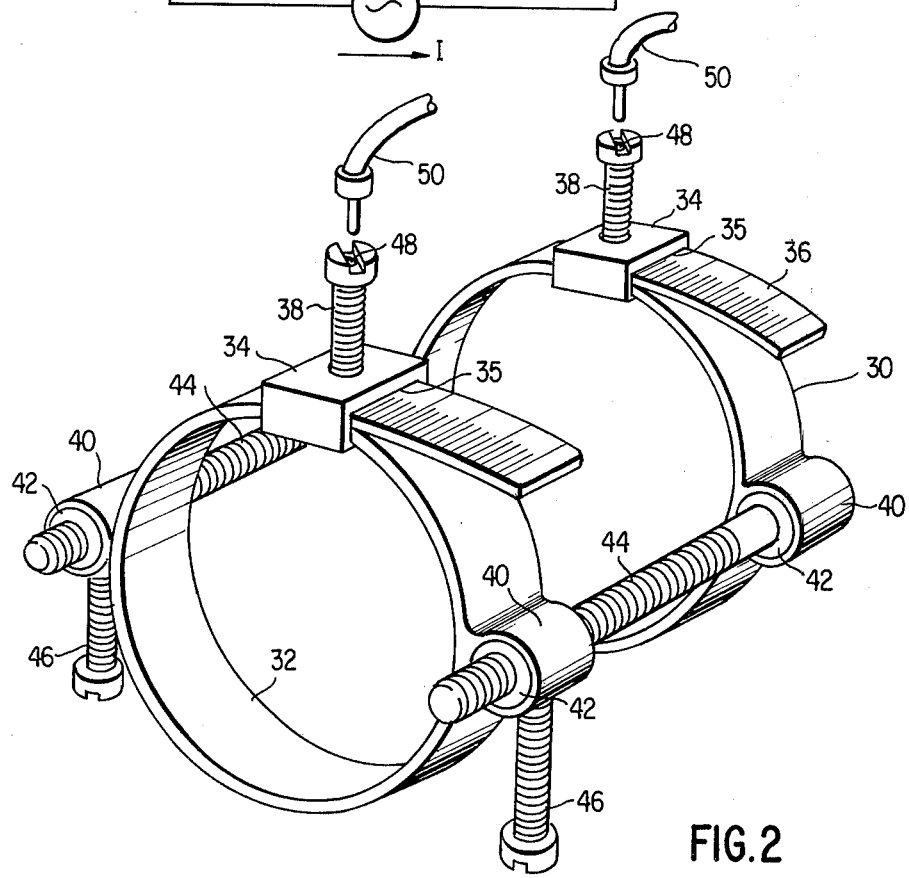
FIG. 2 is a schematic view of a pair of readout ring electrodes which form the subject matter of the present invention.

FIG. 2 illustrates a pair of readout ring electrodes constructed according to the present invention. Electrodes 30 and 32 are constructed from electrical conductive material and include means for adjusting the circumference thereof. A pair of bands 34 respectively encircle electrodes 30 and 32. Adjustment of the circumference of the ring electrodes 30 and 32 is accomplished by means of selective engagement of scribed sections 36 of ring electrodes 30 and 32 by set screws 38 engaged within bands 34 by tapped holes. The edge 35 of each band 34 functions as a reference mark giving a visual indication of the circumference of the ring electrodes 30 and 32. A pair of cylindrical recesses 40 are attached to the outer surface of each ring electrode. Inserted within each of the cylindrical recesses 40 are a pair of nonconductive bushings 42. A pair of rods 44 having first and second ends which are respectively attached to bushings 42 of ring electrodes 30 and 32. The first ends of rods 44 are fixedly attached to bushings 42 of ring electrode 30. The second ends of rods 44 are slidably attached to bushings 42 of ring electrodes 32. The rods 44 have measurement indicia inscribed on their outer surface to permit visual inspection of the axial displacement between the ring electrodes 30 and 32. The rods 44 also provide rigid mounting structure for the two ring electrodes 30 and 32 having a common axis to permit alignment of the ring electrodes 30 and 32 with the axis of the part of the body being encircled thereby. A pair of nonconductive set screws 46 to permit axial adjustment of the position of the ring electrode 30 with respect to ring electrode 32 are engaged within threaded holes tapped through cylindrical recesses 40 and bushings 42 associated with ring electrode 32. The set screws 46 clamp ring electrode 32 in a fixed axial position when they engage the surfaces of rods 44. The bushings 42 and set screws 46 are constructed from nonconductive materials to produce electrical isolation of the first ring electrode 30 from the second ring electrode 32. A pair of cylindrical recesses 48 are bored within the heads of the set screws 38 for permitting coupling of recording leads 50 having male connectors into recesses 48. The recesses 48 and leads 50 including male connectors comprise male contact assemblies.

OPERATIONS

The readout ring electrodes constructed according to the present construction are used as follows. The circumference of the ring electrodes 30 and 32 is adjusted to the appropriate diameter to encircle the finger or other body part being tested for electrical impedance. The set screws 38 are tightened to clamp the ring electrodes 30 and 32 at a desired circumference. The axial displacement between the ring electrodes 30 and 32 is adjusted by loosening set screws 46 and sliding the rods 44 with respect to ring electrode 32 and then tightening set screws 46. The axial displacement of the ring electrodes is adjusted to match average electrical impedance of the body segment being tested with the scale of the impedance meter being used in conjunction with the ring electrodes 30 and 32. A set of leads 50 having male connectors is inserted into the recesses 48 which are cut in the top of set screws 38. The other ends of the leads 50 are connected to an electrical impedance measuring instrument which forms part of an impedance meter of a well known construction which does not form a part of the present invention. The insulative bushings 42 disposed within the cylindrical recesses 40 and the insulative set screws 46 maintain electrical isolation between the two ring electrodes 30 and 32.

The ring electrodes of the present invention may be constructed from any one of the groups of well known conductive materials.

As explained above, bushings 42 and set screws 46 should be constructed from nonconductive materials such as nylon, etc.

While the invention has been described in terms of a preferred embodiment, it should be apparent to those skilled in the art to which the invention pertains, that numerous changes and modifications may be made to the invention without departing from the spirit and scope thereof. It is intended that these modifications fall within the scope of the appended claims.

What I claim as my invention is:

1. An electrode assembly adapted to be used in an apparatus for measuring electric impedance between parts of a living animal comprising:
    a. a first ring electrode having opposite ends which overlap for adjusting the diameter thereof;
    b. a second ring electrode having opposite ends which overlap for adjusting the diameter thereof;
    c. first and second male contact assemblies respectively electrically coupled to said first and second ring electrodes;
    d. means for adjusting the circumference of said ring electrodes, said means comprising:
        1. a band encircling each of said ring electrodes where the ends overlap,
        2. a tapped hole in each of said bands,
        3. a conductive set screw inserted into each of said tapped holes and clamping the overlapping ends of each said ring electrode, said set screws each having an axial hole disposed in the head thereof, and said first and second male contacts being inserted in said axial holes; and
    e. means coupled to each of said rings for maintaining said rings at an adjustable fixed axial position with respect to each other, said means for adjusting axial position being nonconductive for maintaining electrical isolation between said ring electrodes.

2. In an electrode assembly as recited in claim 1 wherein each of said ring electrodes further comprise:
    a. measurement indicia scribed on a surface of said ring for indicating the circumference of said ring.

3. In an electrode assembly as recited in claim 1 wherein said means for adjusting axial position further comprises:
    a. measurement indicia scribed on a surface of said means for adjusting axial position for indicating the axial distance between said ring electrodes.

4. In an electrode assembly as recited in 1 wherein said means for adjusting axial position comprises:
    a. a pair of rods having a pair of first and second ends, said ends of said rods having an outer surface, the first pair of ends of said rods being coupled to said first ring electrode and the second pair of ends of said rods being coupled to said second ring electrode.

5. In an electrode assembly as recited in claim 4 wherein said means for adjusting axial position further comprises:
    a. first and second pairs of cylindrical recesses being joined respectively to said first and second ring electrodes, said cylindrical recesses having an inner cylindrical surface;
    b. said first pair of ends of said rods being inserted in said first pair of cylindrical recesses; and
    c. said second pair of ends of said rods being inserted in said second pair of cylindrical recesses.

6. In an electrode assembly as recited in claim 5 wherein said means for adjusting axial position further comprises:
    a. a first and second pair of nonconductive bushings;
    b. said first pair of bushings being inserted between said outer surface of said first pair of ends of said rods and said inner surface of said first pair of cylindrical recesses; and
    c. said second pair of bushings being inserted between said outer surface of said second pair of ends of said rods and said inner surface of said second pair of cylindrical recesses.

7. In an electrode assembly as recited in claim 6 wherein said means for adjusting axial position further comprises:
    a. a pair of threaded holes respectively tapped through said second pair of cylindrical recesses and said second pair of bushings; and
    b. a pair of set screws inserted into said threaded holes to engage said outer surface of said second pair of ends of said rods to fix the axial position of said electrodes with respect to each other.

* * * * *